US009759834B2

United States Patent
Lee et al.

(10) Patent No.: US 9,759,834 B2
(45) Date of Patent: Sep. 12, 2017

(54) METHOD AND APPARATUS FOR DOWNHOLE PHOTON IMAGING

(71) Applicant: HALLIBURTON ENERGY SERVICES, INC., Houston, TX (US)

(72) Inventors: Dongwon Lee, Kingwood, TX (US); Weijun Guo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/758,695

(22) PCT Filed: Dec. 30, 2013

(86) PCT No.: PCT/US2013/078378
§ 371 (c)(1),
(2) Date: Jun. 30, 2015

(87) PCT Pub. No.: WO2015/102587
PCT Pub. Date: Jul. 9, 2015

(65) Prior Publication Data
US 2016/0291198 A1    Oct. 6, 2016

(51) Int. Cl.
| | | |
|---|---|---|
| *G01V 5/08* | (2006.01) |
| *G01V 5/12* | (2006.01) |
| *E21B 47/00* | (2012.01) |
| *G01T 1/20* | (2006.01) |
| *G01N 23/203* | (2006.01) |

(52) U.S. Cl.
CPC ............ *G01V 5/08* (2013.01); *E21B 47/0005* (2013.01); *G01T 1/2018* (2013.01); *G01V 5/125* (2013.01); *G01N 23/203* (2013.01)

(58) Field of Classification Search
CPC ... G01V 5/04; G01V 5/08; G01V 5/12; G01V 5/125; G01T 1/20; G01T 1/2018
See application file for complete search history.

(56) References Cited

U.S. PATENT DOCUMENTS

| | | |
|---|---|---|
| 2,934,652 A | 4/1960 | Caldwell |
| 4,958,073 A | 9/1990 | Becker et al. |
| 7,224,772 B2 | 5/2007 | Jacobs et al. |
| 7,705,294 B2 | 4/2010 | Ramstad et al. |
| 8,138,471 B1 | 3/2012 | Shedlock et al. |

(Continued)

FOREIGN PATENT DOCUMENTS

WO    2015112118    7/2015

OTHER PUBLICATIONS

Young, PCT Search Report for PCT Application No. PCT/US13/78378 mailed May 1, 2014.

(Continued)

*Primary Examiner* — David Porta
*Assistant Examiner* — Faye Boosalis
(74) *Attorney, Agent, or Firm* — Locke Lord LLP

(57) ABSTRACT

Method and apparatus for downhole photon imaging. The downhole photon imaging apparatus includes a photon source that emits photons; a scintillation device that generates a light signal in response to received photons; a light sensing device coupled with the scintillation device for generating an electronic signal in response to a received light signal; and a collimator coupled with the scintillation device which has a design that allows photons with single Compton backscattering and backscattered at a pre-determined backscattering angle to be detected by the scintillation device.

18 Claims, 3 Drawing Sheets

(56) References Cited

U.S. PATENT DOCUMENTS

2010/0314535 A1     12/2010   Zhang et al.
2011/0029246 A1      2/2011   Nikitin et al.

OTHER PUBLICATIONS

Young, PCT Written Opinion for PCT Application No. PCT/US13/78378 mailed May 1, 2014.
Teague, Philip Neil. "Imaging of Backscattered Ionizing Radiation—A Key Enabler for through Mud Borehole Imaging." Offshore Technology Conference. Offshore Technology Conference, 2011.

METHOD AND APPARATUS FOR DOWNHOLE PHOTON IMAGING

TECHNICAL FIELD OF THE INVENTION

The embodiments disclosed herein relate to downhole imaging and, more particularly, to a method and apparatus for downhole photon imaging.

BACKGROUND OF THE INVENTION

In an oil and gas well, cement between the casing and a borehole is designed to provide zonal isolation in the wellbore. However, liquid contaminants or defect created by volumes of inadequate density might lead to failed isolation. Fixing these defects can be expensive and difficult. Methods and devices for detecting defects in the cement and analyzing the quality of the cement are important to the oil and gas industry. One technique common used is acoustic logging. Acoustic logging detects and assesses the cement behind casing by measuring the acoustic impedance of the cement bonded to the casing. However, conventional acoustic tools are subject to important limitations. For example, acoustic decoupling can be caused by the presence of a microannulus or a shear film coating in the casing. A microannulus is typically a small gap that forms between the casing the surrounding cement. A microannulus may allow the casing to move, thus breaking the bond between the cement and the casing. A microannulus may be partial, or in some instances, it may extend around the entire casing circumference. This may allow undesirable fluid communication between zones. Even newly developed ultrasonic imaging tools, which are based on pulse-echo techniques, are limited when heavy mud or thick casing is used, since the reflected signals die away very quickly. For example, the typical upper limit of the casing thickness allowable in pulse-echo ultrasonic measurement is about 0.59 inch. Therefore, this technique is typically only suitable if the volume of interest is very close to the casing and strongly bonded to the reflective surfaces. Otherwise, such defects may go undetected.

Accordingly, a need exists for an improved downhole imaging method and devices.

BRIEF DESCRIPTION OF THE SEVERAL VIEWS OF THE DRAWING

For a more complete understanding of the disclosed embodiments, and for further advantages thereof, reference is now made to the following description taken in conjunction with the accompanying drawings in which.

DETAILED DESCRIPTION OF THE DISCLOSED EMBODIMENTS

Figure 1:
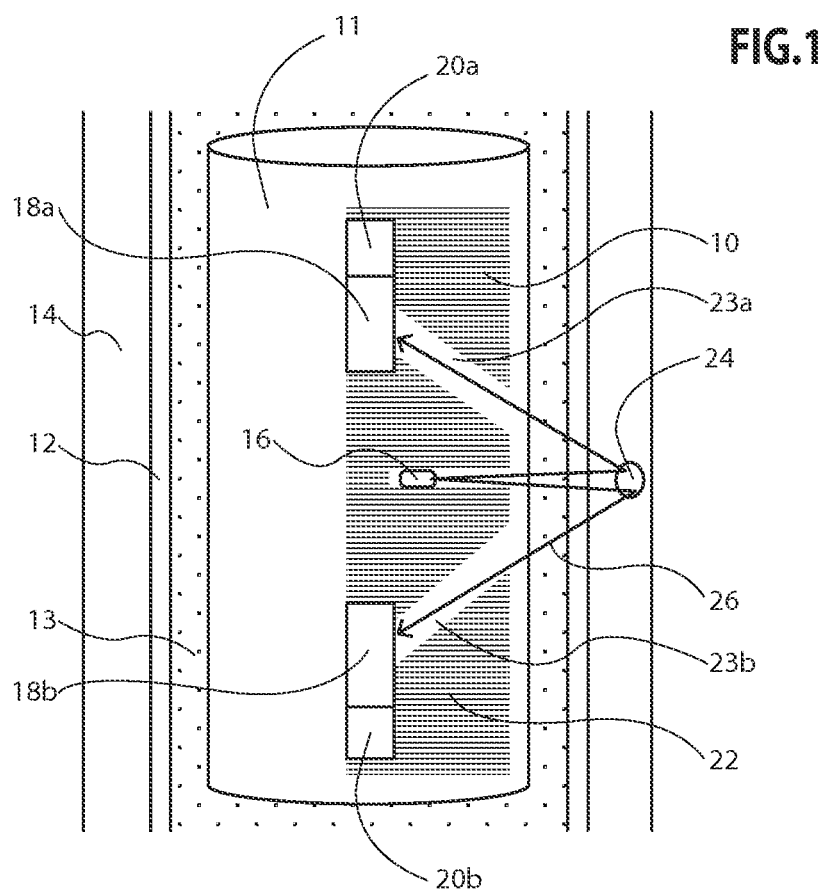
FIG. 1 illustrates a schematic diagram of an apparatus for downhole photon imaging according to the disclosed embodiments.

The following discussion is presented to enable a person skilled in the art to make and use the invention. Various modifications will be readily apparent to those skilled in the art, and the general principles described herein may be applied to embodiments and applications other than those detailed below without departing from the spirit and scope of the disclosed embodiments as defined herein. The disclosed embodiments are not intended to be limited to the particular embodiments shown, but is to be accorded the widest scope consistent with the principles and features disclosed herein.

One embodiment of the invention provides a downhole tool for photon imaging employing a phenomenon known as Compton scattering. The number of backscattered photons coming from an object placed in front of a photon source is a function of photon energy and the backscattering angle. The material properties of the object, such as the attenuation coefficient, and the thickness and density of the object may also affect the number of backscattered photons. Photon attenuation is given by the exponential question $I=I_0 e^{-\mu t}$ where $\mu$ is the linear attenuation coefficient, and is a function of photon energy and the material's density and atomic number. The term $\mu$, is also defined by the sum of the probabilities of photoelectric absorption, Compton scattering and pair production per unit path length that the photon is removed from the beam. The number of backscattered photons depends on the density and length of travel path through the medium and the probability of backscattering at the defect, which is proportional to the atomic number and density of the defect. Thus, non-cement materials like air and water will result in fewer photon counts at the detector.

In downhole applications, the two dominant interactions are photoelectric absorption and Compton scattering. Compton scattering becomes dominant over photoelectric absorption when the photon energy a few hundred kilo-electron volts (keV), for instance, 150-300 keV. In some embodiments the photon energy may be higher, however, for example about 662 keV for a cesium-137 source.

In an embodiment, the photon energy of the emitted photons may be selected to fall within the region where Compton scattering is dominant for the material being imaged. The backscattering angle of the photons detected by the tool may be determined by setting the detector collimator geometry. In this implementation, the number of backscattered and detected photons detected by the downhole tool would be proportional to the density of the cement surrounding the casing, assuming single Compton scattering occurs. Therefore, if the cement has a consistent density, the number of backscattered photons will remain the same; but if there is any density anomaly, the number of backscattered photons will vary, providing an assessment of the density variation in the cement behind the wellbore casing. This allows well engineers to assess the quality of the cement and locate any structural anomalies behind the casing.

Referring to FIG. 1, a schematic diagram of an apparatus 10 for downhole photon imaging of a wellbore casing is illustrated according to one embodiment of the invention. The apparatus 10 is assembled into a downhole tool 11 that can be lowered into a wellbore casing 12 filled with fluid 13. Cement 14 is placed around the casing 12 to provide zonal isolation. Apparatus 10 includes a photon source 16 which emits photons at one or more energy levels or over a broad range of energy levels. Examples of the photon source 16 include chemical sources, such as Cesium-137, induced gamma-rays from or an electronic source, such as an x-ray tube, or in some versions, photons from a neutron-induced source, namely, a material made radioactive through bombardment of neutron flux, could be used. The photon flux may be collimated or focused to define the volume of imaging.

Apparatus 10 further includes two photon detectors 18a and 18b, which may be scintillation devices to produce a light signal in response to received photons. An example of the photon detector 18 suitable for use in embodiments of the invention may be a gamma-ray scintillator or a solid state detector. One particularly useful scintillator in embodiments of the disclosure is as a thallium doped sodium iodide (Nal(Tl)) scintillator. However, it would be apparent to one of ordinary skill in the art that any scintillation device that can generate light signals responsive to collected photons may be employed in the apparatus 10. The photon detectors 18a and 18b in this embodiment are in a cylindrical shape, but other shapes may also be applicable.

The photon detectors in the embodiment shown in FIG. 1 are coupled to a pair of photo-sensors. In this embodiment, photon detector 18a is coupled with the photo-sensor 20a and photon detector 18b is coupled with the photo-sensor 20b. The photon detectors and photo-sensors are advantageously closely coupled together to prevent signal losses. Examples of photo sensors suitable in embodiments of the invention include photomultiplier tubes (PMT) or photodiodes. Other light sensing devices that can generate electrical signals in response to incident light received from the photon detectors 18a and 18b may also be used in alternative embodiments of the apparatus 10 depicted in FIG. 1.

Coupling the photon detectors 18a, 18b to the photo-sensors 20a, 20b may be done in various ways known to those of skill in the art, for example using optical gel or optical pad. For example, fiber optic cables may be used to transmit light generated by the photon detectors to the photo sensors in other embodiments.

In other embodiments, the light transmission between the photon detectors 18a, 18b and the photo-sensors 20a, 20b, may be enhanced or amplified to increase the sensitivity of the apparatus 10, for example, by matching the wavelength of the light produced by the scintillators to the photo-sensor's peak sensitivity and/or by using a reflector material around the scintillator to harvest more light. Although the apparatus shown in FIG. 1 is depicted with a pair of photon detectors and sensors, this is not intended as a limitation, and other embodiments of the invention may be implemented with any number of photon detectors and photo sensors as a matter of design choice.

The apparatus 10 is provided with a housing 22 accommodating the photon source 16, photon detectors 18a, 18b, and photo-sensors 20a, 20b. In one embodiment, the housing 22 is made of shielding material to prevent emitted photons from directly hitting the detectors 18a, 18b directly. The material may have a high atomic number (high-Z), including lead, tantalum and tungsten. This prevents detection of photons that were not backscattered from the area of interest in the cement being analyzed from generating unwanted noise in the photo sensors.

The shielding material is provided with openings or channels 23a and 23b which provide a pathway for photons backscattered from any defect 24 in the area of interest in the cement to reach the photon detectors 18a, 18b. Thus, the shielding is designed to restrict the photons detected by the detectors to the photons that indicate a defect of some sort in the cement and eliminate unwanted photons that are only a source of noise.

The photon source is advantageously placed in the middle of the housing 22, and the two photon detectors 18a and 18b may be disposed symmetrically with respect to the back side of the photon source 16 so that they only receive backscattered photons emitted by the photon source 16. To receive sufficient counts of backscattered photons 29 for assessing the quality of a target object, the photon detectors may be advantageously placed close to the photon source 16, such as within 4-6 inches. As the detectors are placed further from the detectors, the number of detected backscattered photons may be too low to be practical. The number of photons detected should be sufficient so that the statistical uncertainty (measured, for example, by the rms value of the count) drops below a selected threshold level, such as 1% of the count. The measurement time may be varied to achieve the desired threshold.

In another embodiment, the apparatus 10 may be provided with a collimator to assist in the detection of backscattered photons from a target area in the cement surrounding the casing 12. For example, two collimators, each with a cylindrical shape, may be arranged around the two photon detectors 18a and 18b, respectively, with a number of slots on the wall of each collimator to allow backscattered photons to get in the photon detectors. The collimator may further the backscatter angle of the photons that the photon detector can receive. This allows the apparatus to determine the minimum size of the structural anomaly that the apparatus 10 may identify. In one advantageous embodiment, the collimator is designed with a geometry that restricts the detection parameters to photons generated by a single Compton backscattering and from a preselected backscatter angle, while rejecting photons that go through multiple Compton scatterings as much as possible.

While those of skill in the art will understand that it is very difficult to distinguish whether a particular photon has undergone single or multiple Compton scattering events, nevertheless, the collimator may work to detect mostly those photons that have experienced single scattering by using a tight collimator opening. In one embodiment, the openings will match the size of a detector pixel, such as 1 cm×1 cm. In other embodiments, the opening could be even smaller, such as a 1 mm square area, which would increase resolution. Selecting a suitable size and shape for each collimator opening will be within the capabilities of a person skilled in the art depending on the design requirements specified for the tool. As described above, when Compton scattering is dominant and in the case of single Compton scattering, the number of backscattered and detected photons is proportional to the material density of an object in front of a photon source. The backscatter detection angle for the collimator will depend on the application's geometry and may be determined as a matter of design choice. In one practical embodiment, the backscatter angle may range from about 150 to about 120 degrees.

Therefore, apparatus 10 may be used to detect any material density anomaly behind the wellbore casing 12. In one embodiment, if there is a defect in the cement 14, such as a defect 24 filled with fluid or water as illustrated in FIG. 1, the number of the photons backscattered from the region of the defect 24 and detected by the photon detector 18 will be reduced, since the defect 24 has a lower material density compared with the cement. Based on the reduced number of backscattered photons, the defect may be identified and its location may be determined. Of course, it will be understood that while most defects will reduce the photon count, it is possible that some defects, such a metal bolt or nut stuck in the cement could actually increase the photon count.

In another embodiment, the combination of a scintillator and photo-detector may be replaced with a device that detects backscattered photons and directly provides an electrical signal that is proportional to the number of photons detected. For example, in an embodiment, a semiconductor, such as cadmium-zinc-telluride, may be used as a detector.

Figure 2:
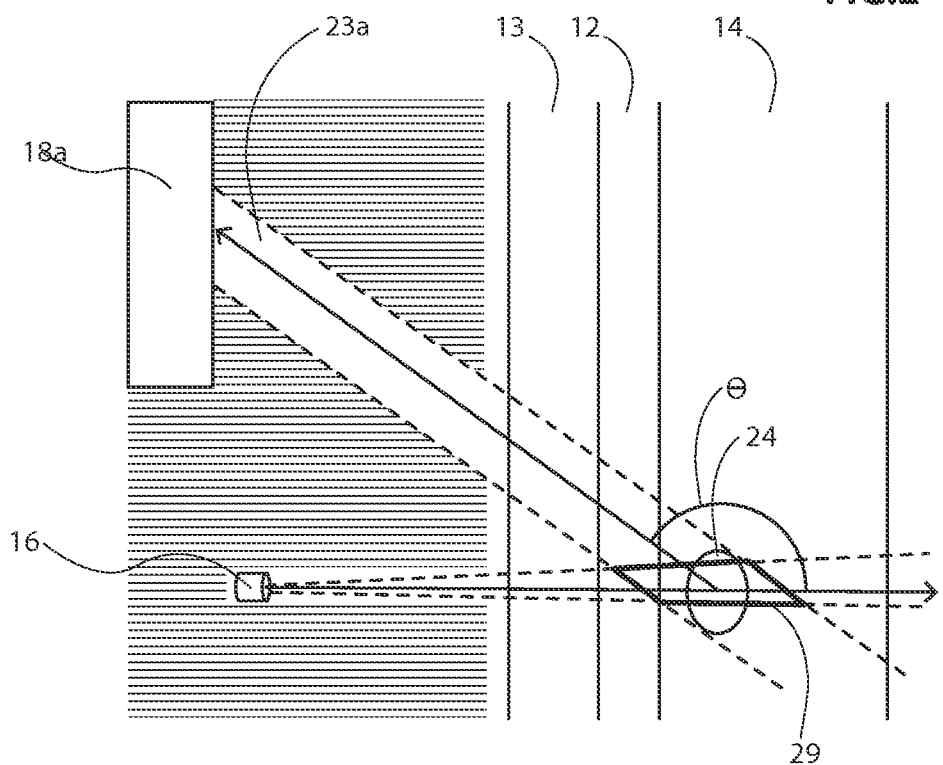
FIG. 2 is a graph illustrating Monte Carlo simulation results of the downhole photon imaging method regarding the relationship between the number of backscattered photons and material density of a target object according to the disclosed embodiments.

FIG. 2 further illustrates how a downhole tool according to embodiments of the invention may operate to detect defects in cement behind the casing. FIG. 2 is an illustrative graph showing a Monte Carlo simulation of the backscattered photons from a 1 $cm^3$ target object that is filled with either air, water or cement. The steel casing simulated was a 0.3 inch thick section. While maintaining the same geometry, as shown in FIG. 1, the defect material was changed to air, water, and cement. In FIG. 2, the points at 0 material density represent air, the points at 1 material density represent water, and the points at 1.8 represent cement. The source was at the origin. The scintillator was 3.5 cm long and its center placed at 4.75 cm above the source. The defect was located immediately behind the casing. No microannulus was included, however, the existence of a typical microannulus, less than 1 mm in thickness, should not affect the result. The area scanned was −1.25 cm to 1.25 cm along with X-axis and Y-axis.

The photon source energy in the simulation was varied from 200 to 662 keV. The horizontal axis represents material density, and the vertical axis represents the counts of backscattered photons detected by a photon detector. The count-material density relationship when the photon source energy is 200 keV, 300 keV, 400 keV and 662 keV, is represented by the lines defined by diamond, square, triangle, and "X" symbols, respectively. As seen from FIG. 2, the number of backscattered and detected photons shows a nearly linear relationship with the density of the materials, regardless of the backscattering is caused by air, water or cement. The difference in the counts of photons for different materials may be used by embodiments of the invention as an indicator of the material density behind the casing. Any microannulus or thin layer of paint or other coating less than 1 mm thick should not contribute to the detector count any more than noise level.

Figure 3:
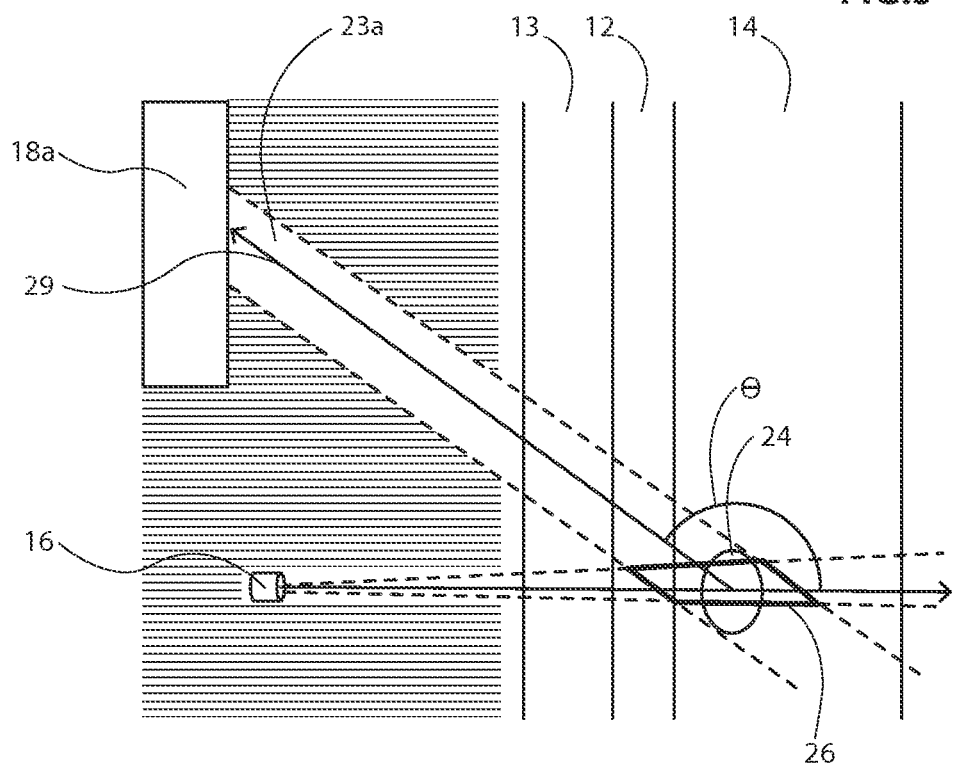
FIG. 3 illustrates a schematic diagram of an enlarged portion of FIG. 1.
Figure 4A:
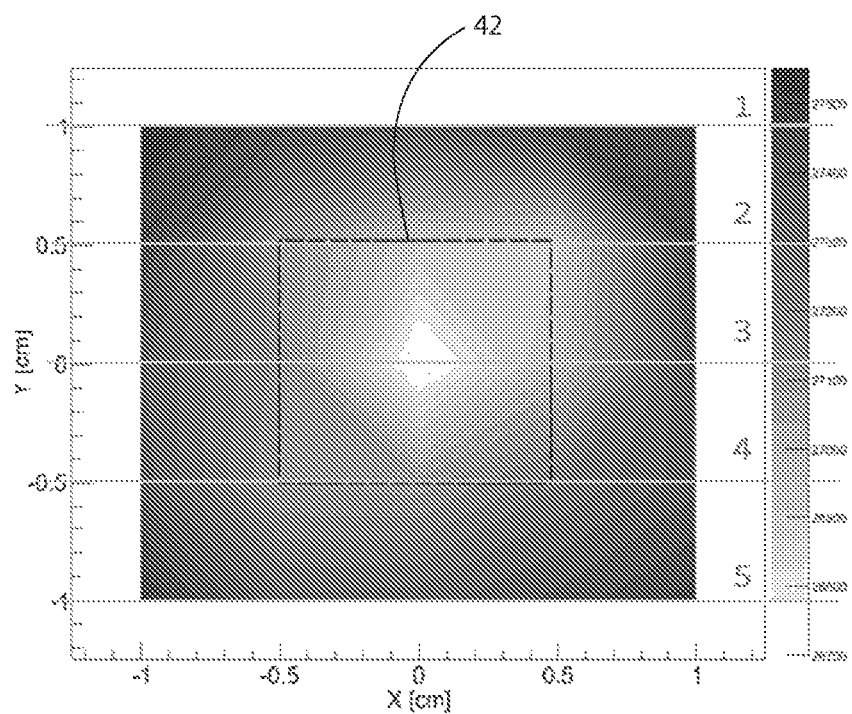
FIG. 4A is a 2-D image illustrating the location of a water defect obtained by use of the downhole photon imaging method according to the disclosed embodiments.
Figure 4B:
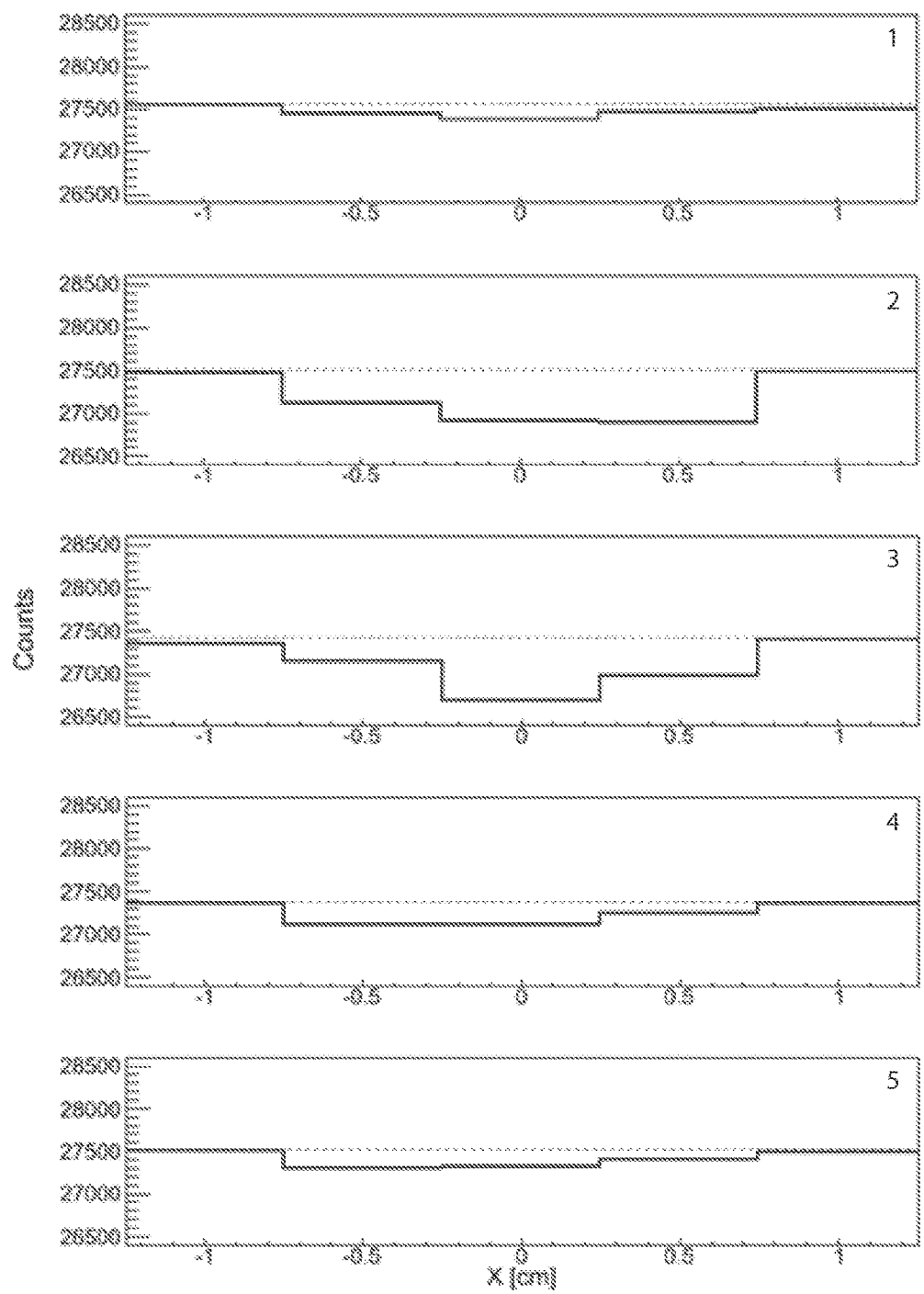
FIG. 4B is a group of 1-D graphs obtained from FIG. 4A along the horizontal axis lines depicted.

FIG. 3 and FIG. 4A-4B illustrate another Monte Carlo simulation environment according to embodiments of the invention. FIG. 3 illustrates an enlarged portion of FIG. 1 showing the photon source 16, photon detector 18a, the casing 12, the fluid 13, the cement 14 and a defect 24 in the cement 14. The simulated defect 24 was a 1 $cm^3$ water cavity located immediately behind a 0.3 inch thickness steel casing 12 and embedded in the cement 14. A 1.62 cm thick water body was used as the fluid 13, and placed between the apparatus 10 and the casing 12. The backscatter angle θ determined by the collimator geometry was 135 degrees. The opening of the collimator is designed to cover cement volume of 2.4 cm in length, with the size of the photon beam spot being one-half by one-half $cm^2$. The volume of investigation is depicted by region 26.

FIG. 4A shows a 2-D raster image reconstructed from the counts of backscattered photons from the simulation depicted in FIG. 3. The image shows the counts detected by the photon detector 18a when the apparatus 10 scanned the area around the water defect 24 with the defect 24 as the scanning center. The photon source energy used to create the image in FIG. 4A was 300 keV. The horizontal axis represents the horizontal scanning range and the vertical axis represents the vertical scanning range of the apparatus according to this embodiment. The dashed line 42 shows the position of a water defect 24 behind the steel casing. The dimensions of the defect 24 were 1 cm for each of the width, length and height of the cube. The imaged was assembled from the results of five scans along the horizontal lines labeled 1-5 from top to bottom on the right-hand side of FIG. 4A. In the illustrative image, a region with low counts will be interpreted as a low density anomaly behind the steel casing signifying a defect other than cement. If there is no defect, the count in each pixel is similar to each adjacent pixel within a statistical uncertainty and the 2-D image should be flat and featureless.

FIG. 4B shows a group of 1-D profiles obtained along the five horizontal scan lines in FIG. 4A. The vertical axis represents the counts of backscattered photons. As can been seen from FIG. 4B, the decreased counts in the center along the 2nd, 3rd and 4th scan lines are due to the water defect. The decrease in counts generally disappears along the 1st and the 5th scan lines. The simulation results show that by relating the material density with the number of backscattered photons, the disclosed embodiments can be used to inspect the quality of structure behind a borehole casing, and an image of the structure density can be obtained through density mapping by use of the photon counts.

In operation, the apparatus 10 may be lowered down into a borehole casing, moved up or down at a particular depth, and rotated to get the photon measurements of the structures behind the casing. In one embodiment, the apparatus may be rotated at a speed of 10-16 revolutions per minute. Generally, the slower the apparatus is moved along the casing or rotated, the more accurate the photon counts are likely to be. In one embodiment, the number of photons backscattered is measured in real time in the casing, and the data is transmitted to the surface for analysis. In other embodiments, the information may be recorded onto a suitable recording medium, such as electronic memory, and retrieved from the tool at the surface for later analysis.

Embodiments of the invention may be fabricated in a compact apparatus, and can work with Wireline and Slick Line systems. It will also be understood that higher photon source energies can be used to obtain downhole imaging in the case of thicker casing and/or heavy mud without affecting imaging performance.

Any density anomaly in the structure behind the casing may also be observed by density mapping. This requires only the total counts of backscattered photons from the photon detectors. Further, the disclosed apparatus may use electronic photon source or tunable photon source energy, such as an x-ray tube, which may be preferable in some instances over radioactive sources.

In another embodiment, the invention provides an apparatus for downhole photon imaging that includes a photon source that emits photons, a scintillation device that generates a light signal in response to received photons, the scintillation device being positioned so that it only receives backscattered photons emitted from the photon source, a light sensing device coupled with the scintillation device, in which the light sensing device generates an electronic signal in response to a received light signal, and a collimator coupled with the scintillation device. The collimator, in this embodiment allows photons altered by single Compton backscattering and which have been backscattered at a preselected angle to be detected by the scintillation device.

In a further embodiment, the invention provides a method for downhole photon imaging that includes providing a downhole photon imaging apparatus down in a borehole casing. The downhole photon imaging apparatus in this embodiment includes a photon source emitting photons down a borehole, a scintillation device that generates a light signal in response to received photons. The scintillation device may be positioned so that it only receives backscattered photons emitted from the photon source. The apparatus also includes a light sensing device coupled with the scintillation device in which the light sensing device is capable of generating an electronic signal in response to a received light signal, and a collimator coupled with the scintillation device, in which the collimator allows photons with single Compton backscattering and that have been backscattered at a pre-determined backscattering angle to be detected by the scintillation device. The method may also include moving the downhole photon imaging apparatus in the borehole casing to scan a target object of interest.

While particular aspects, implementations, and applications of the present disclosure have been illustrated and described, it is to be understood that the present disclosure is not limited to the precise construction and compositions disclosed herein and that various modifications, changes, and variations may be apparent from the foregoing descriptions without departing from the spirit and scope of the disclosed embodiments as defined in the appended claims.

What is claimed is:

1. An apparatus for downhole photon imaging, comprising:
    a photon source that emits photons;
    a pair of scintillation devices that generates a light signal in response to received photons, the pair of scintillation devices disposed symmetrically about the photon source, each scintillation device being positioned so that it only receives backscattered photons emitted from the photon source;
    a light sensing device coupled with each scintillation device, the light sensing device generating an electronic signal in response to a received light signal; and
    a collimator coupled with each scintillation device, the collimator having a design that allows photons with single Compton backscattering and backscattered at a pre-determined backscattering angle to be detected by the scintillation device.

2. The apparatus of claim 1, further comprising a housing containing the photon source, the scintillation device, the light sensing device and the collimator.

3. The apparatus of claim 1, wherein the photon source comprises a chemical source Cs-137, induced gamma-rays from neutron activation or an electronic source.

4. The apparatus of claim 1, wherein the photon source comprises an x-ray tube.

5. The apparatus of claim 1, wherein the photon source emits photons at one or more energy levels, or over a range of energy levels.

6. The apparatus of claim 1, wherein the scintillation device comprises a gamma-ray scintillator or a solid state detector.

7. The apparatus of claim 1, wherein the light sensing device comprises a photomultiplier or a photodiode.

8. The apparatus of claim 1, further comprising means to enhance light transmission between the scintillation device and the light sensing device.

9. The apparatus of claim 1, wherein the distance between the photon source and the scintillation device is less than 12 inches.

10. A method for downhole photon imaging, comprising:
    providing a downhole photon imaging apparatus in a borehole casing, the downhole photon imaging apparatus comprising:
    a photon source emitting photons;
    a pair of scintillation devices that generates a light signal in response to received photons, the pair of scintillation devices disposed symmetrically about the photon source, each scintillation device being positioned so that it only receives backscattered photons emitted from the photon source;
    a light sensing device coupled with each scintillation device, the light sensing device generating an electronic signal in response to a received light signal;
    a collimator coupled with each scintillation device, the collimator having an design that allows photons with single Compton backscattering and backscattered at a pre-determined backscattering angle to be detected by the scintillation device; and
    moving the downhole photon imaging apparatus in the borehole casing to scan a target object of interest.

11. The method of claim 10, wherein the downhole photon imaging apparatus further comprises a housing containing the photon source, the scintillation device, the light sensing device and the collimator.

12. The method of claim 10, wherein the photon source comprises a chemical source Cs-137, induced gamma-rays from neutron activation or an electronic source.

13. The method of claim 10, wherein the photon source comprises an x-ray tube.

14. The method of claim 10, wherein the photon source emits photons at one or more energy levels, or over a range of energy levels.

15. The method of claim 10, wherein the scintillation device comprises a gamma-ray scintillator or a solid state detector.

16. The method of claim 10, wherein the light sensing device comprises a photomultiplier or a photodiode.

17. The method of claim 10, wherein the downhole photon imaging apparatus further comprises means to enhance light transmission between the scintillation device and the light sensing device.

18. The method of claim 10, wherein the distance between the photon source and the scintillation device is less than 12 inches.

* * * * *